United States Patent
Ge et al.

(10) Patent No.: US 10,139,375 B2
(45) Date of Patent: Nov. 27, 2018

(54) METHODS AND SYSTEMS FOR MONITORING QUALITY OF HYDRAULIC FLUID IN ELECTRO-HYDRAULIC (EH) VALVE

(71) Applicant: Caterpillar Inc., Peoria, IL (US)

(72) Inventors: Xinyu Ge, Peoria, IL (US); Hua Gu, Berrien Springs, MI (US)

(73) Assignee: Caterpillar Inc., Deerfield, IL (US)

( * ) Notice: Subject to any disclaimer, the term of this patent is extended or adjusted under 35 U.S.C. 154(b) by 92 days.

(21) Appl. No.: 15/253,911

(22) Filed: Sep. 1, 2016

(65) Prior Publication Data
US 2018/0059069 A1 Mar. 1, 2018

(51) Int. Cl.
| | |
|---|---|
| *G01N 29/34* | (2006.01) |
| *G01N 29/036* | (2006.01) |
| *G01N 29/032* | (2006.01) |
| *F16K 37/00* | (2006.01) |
| *F16K 11/07* | (2006.01) |

(52) U.S. Cl.
CPC .............. *G01N 29/34* (2013.01); *F16K 11/07* (2013.01); *F16K 37/005* (2013.01); *F16K 37/0091* (2013.01); *G01N 29/032* (2013.01); *G01N 29/036* (2013.01); *G01N 2291/012* (2013.01); *G01N 2291/022* (2013.01)

(58) Field of Classification Search
CPC .... F16K 11/07; F16K 37/005; F16K 37/0091; G01N 29/02–29/036; G01N 29/227; G01N 29/34
See application file for complete search history.

(56) References Cited

U.S. PATENT DOCUMENTS

| | | | | |
|---|---|---|---|---|
| 3,827,335 | A | * 8/1974 | Lewis | F15B 13/0402 91/3 |
| 4,785,287 | A | * 11/1988 | Honma | G01N 29/02 340/631 |
| 6,155,654 | A | * 12/2000 | Oyama | B60T 8/36 137/14 |
| 6,536,390 | B2 | * 3/2003 | Takahashi | F01L 1/022 123/90.15 |

(Continued)

FOREIGN PATENT DOCUMENTS

| | | |
|---|---|---|
| CN | 103867535 | 5/2016 |
| WO | 9801739 | 1/1998 |

*Primary Examiner* — Justin Olamit
(74) *Attorney, Agent, or Firm* — James S. Bennin

(57) ABSTRACT

A method for monitoring quality of a hydraulic fluid in an electro-hydraulic (EH) valve is disclosed. The method includes applying predetermined signal to a solenoid coil, surrounding a pusher pin in EH valve, to facilitate oscillation of a pusher pin in EH valve to change static friction between the pusher pin and a cavity of EH valve, to dynamic friction. EH valve includes a housing defining the cavity having an end wall. Cavity slidably receiving the pusher pin having a first end and a second end. The hydraulic fluid is received between the first end of the pusher pin and the end wall. The oscillation of the pusher pin generates an acoustic wave that propagates through the hydraulic fluid. The method further includes determining the quality of the hydraulic fluid based on one or more characteristics of the acoustic wave detected by an acoustic sensor positioned on the end wall.

20 Claims, 6 Drawing Sheets

(56) References Cited

U.S. PATENT DOCUMENTS

| | | | |
|---|---|---|---|
| 7,159,506 B2* | 1/2007 | Tokura | F15B 11/028 60/329 |
| 7,192,005 B2* | 3/2007 | Denyer | F16K 31/0613 137/625.64 |
| 7,219,536 B2* | 5/2007 | Liu | G01N 11/00 73/10 |
| 7,293,450 B2 | 11/2007 | Lui et al. | |
| 8,118,058 B2* | 2/2012 | Cook | F15B 13/0402 137/625.64 |
| 2014/0182381 A1 | 7/2014 | Comeaux et al. | |
| 2015/0198241 A1* | 7/2015 | Barngrover | F16H 61/0251 137/1 |
| 2016/0138624 A1 | 5/2016 | Oftelie | |

* cited by examiner

METHODS AND SYSTEMS FOR MONITORING QUALITY OF HYDRAULIC FLUID IN ELECTRO-HYDRAULIC (EH) VALVE

TECHNICAL FIELD

The present disclosure relates to an electro-hydraulic (EH) valve. More specifically, the present disclosure relates to methods and systems for monitoring quality of a hydraulic fluid in an EH valve.

BACKGROUND

An electro-hydraulic (EH) valve is usually used to control the flow of hydraulic fluid in various hydraulic systems. For example, the EH valve may be utilized in a transmission system of a machine to control the flow of hydraulic oil in the transmission system. In another example, the EH valve may be utilized in a steering assembly of the machine to control the operation of the steering system. Due to wear and tear in such hydraulic systems, the quality of the hydraulic fluids, being circulated in such hydraulic systems, may degrade with time and usage of the machine. Other factors that may affect the quality of the hydraulic fluid may include, but are not limited to, oxidation of the hydraulic fluid, contamination of the hydraulic fluid, and consumption of additives by the hydraulic fluid. Contaminated hydraulic fluids may damage the EH valve.

Usually, the contamination of the hydraulic fluid in the hydraulic systems is monitored using a light source and photo detectors. The light source may be installed at one end of a flow path in the hydraulic system, and the photo detector may be installed at another end of the flow path. A beam of light is directed through the hydraulic fluid and its intensity is monitored by the photodetector to determine the level of contaminants in the hydraulic fluid. However, integrating light sensors (or photodetectors) in the hydraulic system flow paths may increase the complexity and a cost of the hydraulic systems.

PCT patent application WO9801739A2 (hereinafter referred to as '739) discloses a system to detect a quality of lubricating oil in an oil pan. An acoustic sensor, installed in the oil pan, includes a piezoelectric element that is configured to generate a wave signal. The wave signal propagates through the oil and is detected by the acoustic sensor. Based on the wave detected by the acoustic sensor, the quality of the oil is determined. However, the system disclosed in '739 requires a separate wave generating device and a separate sensor device. Accordingly, integrating such a system in hydraulic systems is complex (due to space constraints) and expensive.

SUMMARY

According to an aspect of the disclosure, a method for monitoring a quality of a hydraulic fluid in an electro-hydraulic (EH) valve, is disclosed. The method includes applying a predetermined signal to a solenoid coil, surrounding a pusher pin in the EH valve, to facilitate oscillation of the pusher pin to change static friction between the pusher pin and a cavity of the EH valve, to dynamic friction. The EH valve includes a housing defining the cavity having an end wall. The cavity slidably receiving the pusher pin having a first end and a second end. The hydraulic fluid is received between the first end of the pusher pin and the end wall. The oscillation of the pusher pin generates an acoustic wave that propagates through the hydraulic fluid. The method further includes determining the quality of the hydraulic fluid based on one or more characteristics of the acoustic wave detected by an acoustic sensor positioned on the end wall.

According to another aspect of the disclosure an electro-hydraulic (EH) valve is disclosed. The EH valve includes a housing defining a cavity having an end wall. The EH valve further includes a pusher pin slidably received in the cavity. The pusher pin having a first end and a second end. The first end of the pusher pin is proximate to the end wall. A hydraulic fluid is receivable between the first end of the pusher pin and the end wall. The EH valve further includes an acoustic sensor disposed on the end wall. A solenoid coil surrounds the pusher pin. An actuation of the solenoid coil controls a movement of the pusher pin in the cavity. The solenoid coil being configured to receive a predetermined signal to facilitate oscillation of the pusher pin to change static friction between the pusher pin and a cavity of the EH valve, to dynamic friction. The oscillation of the pusher pin generates an acoustic wave that propagates through the hydraulic fluid. The acoustic sensor is configured to detect the acoustic wave through the hydraulic fluid. A quality of the hydraulic fluid is determined based on one or more characteristics of the acoustic wave detected by the acoustic sensor.

According to yet another aspect of the disclosure an electro-hydraulic (EH) valve system for monitoring a quality of a hydraulic fluid used in the EH valve system, is disclosed. The EH valve system includes an EH valve that further includes a housing defining a cavity having an end wall. A pusher pin slidably received in the cavity. The pusher pin having a first end and a second end. The first end of the pusher pin is proximate to the end wall. The hydraulic fluid is receivable between the first end of the pusher pin and the end wall. An acoustic sensor disposed on the end wall. The EH valve further includes a solenoid coil surrounding the pusher pin. An actuation of the solenoid coil controls a movement of the pusher pin in the cavity. A controller communicatively coupled to the acoustic sensor, the controller being configured to apply a predetermined signal to the solenoid coil to facilitate oscillation of the pusher pin to change static friction between the pusher pin and a cavity of the EH valve, to dynamic friction. The oscillation of the pusher pin generates an acoustic wave that propagates through the hydraulic fluid. The controller is further configured to receive a voltage signal, from the acoustic sensor, corresponding to the acoustic wave detected by the acoustic sensor. The controller may be further configured to determine one or more characteristics of the acoustic wave based on one or more characteristics of the voltage signal. The quality of the hydraulic fluid is determined by the controller based on the one or more characteristics of the acoustic wave.

DETAILED DESCRIPTION

Figure 1:
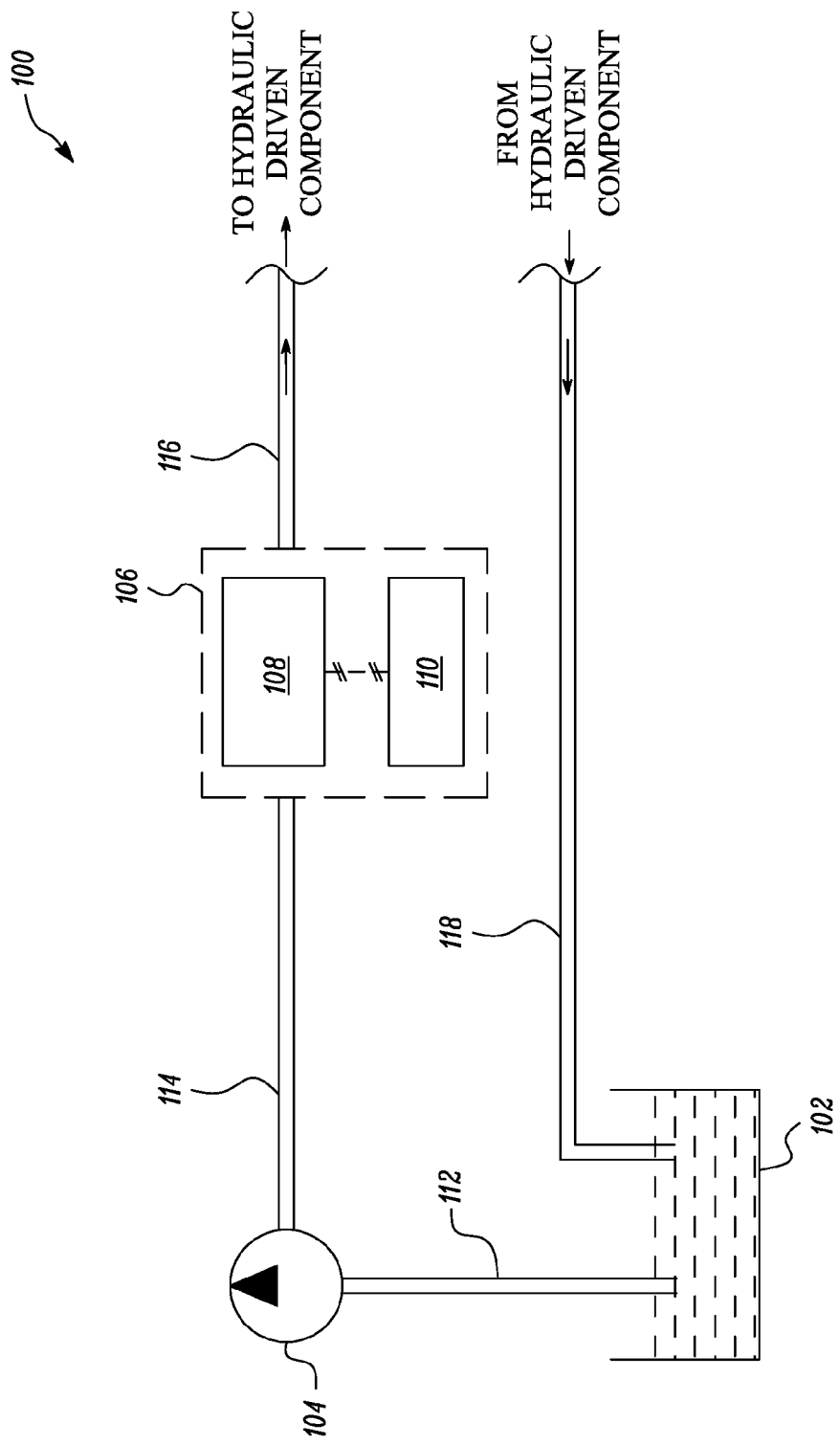
FIG. 1 illustrates a schematic of a hydraulic system, in accordance with certain implementations of the present disclosure.

FIG. 1 illustrates a schematic of a hydraulic system 100, in accordance with certain implementations of the present disclosure. The hydraulic system 100 includes a reservoir 102, a pump 104, and an electro-hydraulic (EH) valve system 106. In certain implementations, the EH valve system 106 may include an EH valve 108, and a controller 110.

The reservoir 102 may store a hydraulic fluid that may be circulated in the hydraulic system 100. The reservoir 102 may be fluidly coupled to an inlet of the pump 104 through a first conduit 112. An outlet of the pump 104 may be fluidly coupled to the EH valve 108, in the EH valve system 106, through a second conduit 114. In certain implementations, the pump 104 may correspond to a hydraulic pump that may have a capability to pump the hydraulic fluid from the reservoir 102 to the various components of the hydraulic system 100, for example the EH valve 108. The EH valve 108 may be further fluidly coupled to a hydraulic driven component (not shown) through a third conduit 116 to supply the hydraulic fluid to the hydraulic driven component. In certain implementations, the hydraulic fluid from the hydraulic driven component may be supplied back to the reservoir 102 through a fourth conduit 118. In certain implementations, the hydraulic driven component may be operated by the hydraulic fluid. Some examples of the hydraulic driven component may include, but are not limited to, an implement of a machine, a transmission system of the machine, and/or the like.

In certain implementations, the EH valve 108 may be configured to control a flow of the hydraulic fluid to the hydraulic driven component. In certain implementations, the EH valve 108 may operate in one or more configurations that may be deterministic of a flow rate of the hydraulic fluid supplied to the hydraulic driven component. For example, in a first configuration of the one or more configurations, the EH valve 108 may allow the hydraulic fluid to flow to the hydraulic driven component, facilitating an operation of the hydraulic driven component. In a second configuration of the one or more configurations, the EH valve 108 may block the flow of the hydraulic fluid to the hydraulic driven component, and therefore may halt the operation of the hydraulic driven component.

A person having ordinary skills in the art would appreciate that the scope of the disclosure is not limited to operating the EH valve 108 to allow the hydraulic fluid flow in the first configuration and block the hydraulic fluid flow in the second configuration. In certain implementations, an operation of the EH valve 108 may allow the hydraulic fluid flow in the second configuration and may block the hydraulic fluid flow in the first configuration. In other configurations of the one or more configurations, the EH valve 108 may alter a flow rate of the hydraulic fluid being delivered to the hydraulic driven component. In certain implementations, the EH valve 108 may be a 2-way valve, a 3-way valve or any other type of valve that may be capable of allowing the hydraulic fluid to flow to the hydraulic driven component. The structure and operation of the EH valve 108 has been described in conjunction with FIG. 2.

Figure 2:
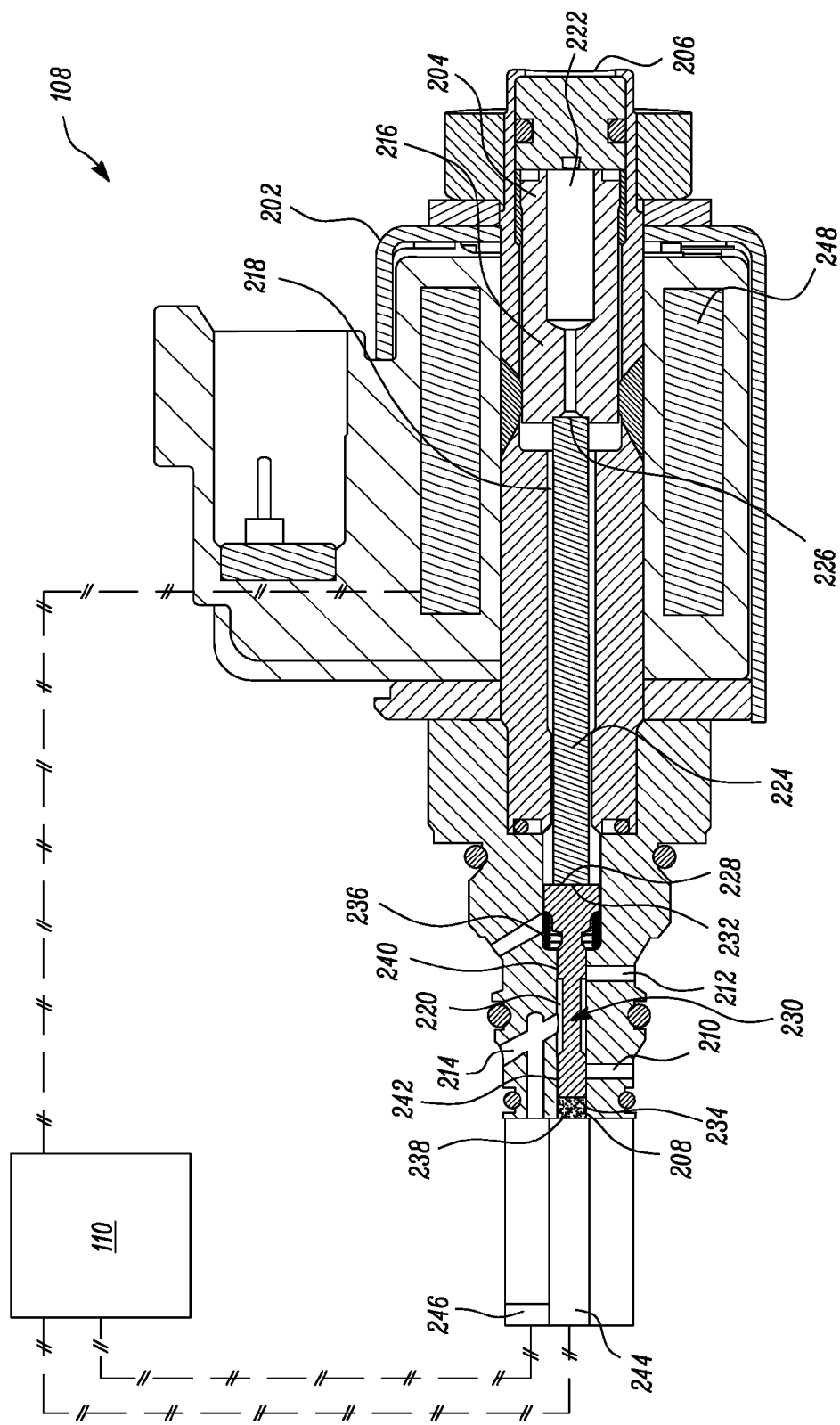
FIG. 2 is a diagrammatic illustration of an Electro-Hydraulic valve system, in accordance with certain implementations of the present disclosure.

Referring to FIG. 2, the EH valve 108 may include a housing 202. The housing 202 may define a cavity 204 that may have a first end wall 206 and a second end wall 208. The housing 202 may further define one or more fluid paths, for example a first fluid path 210, a second fluid path 212, and a third fluid path 214. In some implementations, the first fluid path 210 may be fluidly coupled to the outlet of the pump 104 through the second conduit 114. The second fluid path 212 may be fluidly coupled to the reservoir 102. Further, the third fluid path 214 may be fluidly coupled to the hydraulic driven component through the third conduit 116. A person having ordinary skills in the art would appreciate that the scope of the disclosure is not limited to the EH valve 108 that has three fluid paths. In certain implementations, the EH valve 108 may have more than three fluid paths based on the application for which the EH valve 108 has been designed.

Further, the cavity 204 may include a first annular portion 216, a second annular portion 218, and a third annular portion 220. In some implementations, a diameter of the first annular portion 216 may be greater than a diameter of the second annular portion 218 and a diameter of the third annular portion 220. Further, the diameter of the second annular portion 218 may be greater than the diameter of the third annular portion 220. Additionally, the first annular portion 216 may open into the second annular portion 218 that may further open into the third annular portion 220.

In some implementations, the first annular portion 216 may be configured to receive an armature 222. Further, the second annular portion 218 may be configured to slidably receive a pusher pin 224. The pusher pin 224 may include a first end 226 and a second end 228. In some implementations, the first end 226 of the pusher pin 224 may be in contact with the armature 222, and the second end 228 of the pusher pin 224 may be proximate to the second end wall 208 of the cavity 204. In certain implementations, the pusher pin 224 may move in a horizontal direction relative to the EH valve 108 based on the actuation of the armature 222. A person having ordinary skills in the art would appreciate that the movement of the pusher pin 224 in the horizontal direction is due to the orientation of the EH valve 108 as illustrated in the FIG. 2. If the orientation of the EH valve 108 is rotated by 90 degrees, the movement of the pusher pin 224 may be in the vertical direction. For the purpose of the ongoing description, the orientation of the EH valve 108 has been considered as illustrated in FIG. 2. However, the scope of the disclosure should not be limited to the illustrated orientation.

In some implementations, the third annular portion 220 may be configured to slidably receive a spool 230. The spool 230 may include a first end 232 and a second end 234. In some implementations, a portion of the spool 230 may extend into the second annular portion 218. The portion of the spool 230 that may extend in the second annular portion 218 may form the first end 232 of the spool 230 and may be in contact or in abutment with the second end 228 of the pusher pin 224. In some implementations, a resilient member 236 may be positioned between an end wall of the second annular portion 218 and the portion of the spool 230 in the second annular portion 218. In some implementations, the movement of the spool 230 may be controlled based on the movement of the pusher pin 224 and the resilient member 236. Further, the second end 234 of the spool 230 may be proximate to the second end wall 208 of the cavity 204. In some implementations, a gap 238 may be defined between the second end 234 of the spool 230 and the second end wall 208 of the cavity 204. In some implementations, the spool 230 may have a first portion 240 and a second portion 242. The first portion 240 may be configured to selectively cover the second fluid path 212 to control the flow of the hydraulic fluid to/from the second fluid path 212. Similarly, the second portion 242 may be configured to selectively cover the first fluid path 210 to control the flow of the hydraulic fluid to/from the first fluid path 210. A person having ordinary skills in the art would appreciate that the scope of the disclosure is not limited to having two portions for selectively covering the first fluid path 210 and the second fluid path 212. In certain implementations, multiple portions may be defined on the spool 230 when more than three fluid paths are defined in the housing 202 of the EH valve 106. A person having ordinary skills in the art would appreciate that the scope of the disclosure is not limited to having a pusher pin 224 separate from the spool 230. In certain implementations, the spool 230 and the pusher pin 224 may be integrally formed, without departing from the scope of the disclosure. In such a scenario, the pusher pin 224 may have a first portion and a second portion. The first portion of the pusher pin may be the spool 230 that may be proximate to the second end wall 208 of the cavity 204. The second portion may be in contact with the armature 222.

The second end wall 208 of the cavity 204 may receive an acoustic sensor 244 and a temperature sensor 246. In some implementations, the second end wall 208 may have a recess that may be configured to receive the acoustic sensor 244 and the temperature sensor 246. The acoustic sensor 244 may include a circuitry that may be configured to detect an acoustic wave. In certain implementations, the acoustic sensor 244 may be configured to generate a voltage signal based on a detected acoustic wave. Further, the acoustic sensor 244 may transmit the voltage signal to the controller 110. In some implementations, the acoustic sensor 244 may include a piezoelectric crystal that may have the capability to generate the voltage signal on detection of the acoustic wave. However, the scope of the disclosure should not be limited to the acoustic sensor 244 having the piezoelectric crystal. Some other examples of the acoustic sensor 244 may include, but are not limited to, a thickness-shear mode (TSM) resonator, a surface acoustic wave (SAW) sensor, an acoustic plate mode (APM) sensor, or a flexural plate-wave (FPW) sensor.

The temperature sensor 246 may include a circuitry that may be configured to measure the temperature of the hydraulic fluid flowing through the EH valve 106. Further, the temperature sensor 246 may transmit a value of the temperature to the controller 110. Examples of the temperature sensor 246 may include, but are not limited to, a thermistor, a thermocouple, a resistance thermometer, a silicon band gap thermometer, and the like.

The housing 202 may further include a solenoid coil 248 that may be positioned in the housing 202 in such a manner that the solenoid coil 248 surrounds the first annular portion 216 and the second annular portion 218. In certain implementations, the solenoid coil 248 may surround a section of the first annular portion 216 and a section of the second annular portion 218. Therefore, the solenoid coil 248 may surround the armature 222 and the pusher pin 224 in the first annular portion 216 and the second annular portion 218, respectively. In other implementations, the solenoid coil 248 may only surround the first annular portion 216. The solenoid coil 248 may be coupled to the controller 110. In some implementations, the solenoid coil 248 may be configured to control the movement of the armature 222, positioned in the first annular portion 216, based on a reception of a signal from the controller 110. A person having ordinary skills in the art would appreciate that the scope of the disclosure is not limited to the solenoid coil 248 receiving the signal from the controller 110. In some implementations, the EH valve system 106 may include a signal generator that may generate and transmit the signal to the solenoid coil 248 based on an instruction received from the controller 110.

In some implementations, the signal applied to the solenoid coil 248 may be at least one of a predetermined signal or an actuation signal. In certain implementations, the predetermined signal may be a signal that may facilitate oscillation of the armature 222. The oscillation of the armature 222 may cause the pusher pin 224 to oscillate that in turn may cause the spool 230 to oscillate. In certain implementations, a magnitude of the predetermined signal may allow the spool 230 to oscillate without altering the fluid connectivity between the one or more fluid paths defined in the housing 202. Continuous oscillations of the spool 230 and the pusher pin 224 may change the static friction, between the spool 230 and the cavity 204, and between the pusher pin 224 and the cavity 204, respectively, to the dynamic friction. Hereinafter, the predetermined signal may be referred to a predetermined dither signal.

In some implementations, the actuation signal may correspond to a signal that may be applied to the solenoid coil 248 to facilitate movement of the pusher pin 224 and the spool 230 in the cavity 204. The movement of the spool 230 may control fluid connectivity among the one or more fluid paths. In some implementations, a magnitude of the actuation signal may determine an amount by which the spool 230 moves in the cavity 204. A position of the spool 230 in the cavity 204 may determine a configuration of the EH valve 108 that may be further deterministic of the fluid connections among the one or more fluid paths in the EH valve 108.

For example, the actuation signal of a first magnitude may cause the spool 230 to move to a position that may fluidly couple the first fluid path 210 to the third fluid path 214. Further, the first portion 240 of the spool 230 may completely cover the second fluid path 212 to block the hydraulic fluid flow to/from the second fluid path 212. In such a configuration, the hydraulic fluid may flow from the first fluid path 210 to the third fluid path 214. Additionally, the hydraulic fluid may flow into the gap 238 between the second end 234 of the spool 230 and the second end wall 208 of the cavity 204. Hereinafter, the configuration, in which the first fluid path 210 is fluidly coupled to the third fluid path 214, and the fluid flow to/from the second fluid path 212 is blocked, may be referred to as a first configuration of the EH valve 108.

In another example, the actuation signal of a second magnitude may cause the spool 230 to move to a position where the first portion 240 of the spool 230 may completely cover the second fluid path 212 and the second portion 242 of the spool 230 may completely cover the first fluid path 210. Therefore, the spool 230 may block the fluid flow between the first fluid path 210 and the third fluid path 214. Further, the spool 230 may block the fluid flow between the third fluid path 214 and the second fluid path 212. In such a configuration, the hydraulic fluid in the gap 238 may be retained (as the first portion 240 of the spool 230 may completely cover the second fluid path 212). Hereinafter, the configuration, in which the fluid flow from the first fluid path 210 to the third fluid path 214 is blocked, and the hydraulic fluid in the gap 238 is retained, may be referred to as a second configuration of the EH valve 108.

In yet another example, when the actuation signal is not applied, the spool 230 may move right to a default position due to expansion of the resilient member 236. The default position of the spool 230 is such that the second fluid path 212 may connect to the third fluid path 214. Further, the spool 230 may block the fluid flow between the first fluid path 210 and the third fluid path 214. Further, in such configuration, the hydraulic fluid in the gap 238 may flow out through the second fluid path 212. Hereinafter, the configuration, in which the third fluid path 214 is fluidly coupled with the second fluid path 212, and the hydraulic fluid in the gap 238 drains out from the second fluid path 212, has been referred to as a third configuration of the EH valve 108.

A person having ordinary skills in the art would appreciate that the scope of the disclosure is not limited to the aforementioned configurations of the EH valve 108. In some implementations, the EH valve 108 may be configured to operate in the one or more configurations, without departing from the scope of the disclosure.

In some implementations, the controller 110 may control the operation of the EH valve 108 by the application of the predetermined dither signal and the actuation signal. Further, the controller 110 may be communicatively coupled to the acoustic sensor 244 and the temperature sensor 246. In some implementations, the controller 110 may include a processor and a memory. The processor may include suitable circuitry that is capable of executing computer readable instructions stored in the memory to perform predetermined operation. For example, the processor may be configured to execute the computer readable instructions to control the operation of the EH valve 108. Further, the controller 110 may be configured to execute the computer readable instructions to monitor a quality of the hydraulic fluid in the gap 238. Monitoring of the quality of the hydraulic fluid will be described in conjunction with FIG. 3 and FIG. 4.

Figure 3:
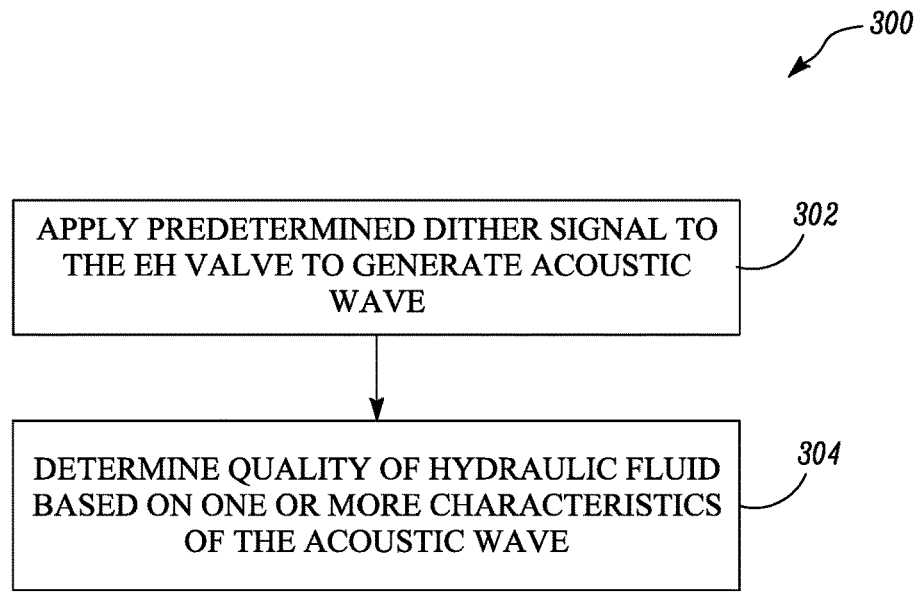
FIG. 3 illustrates a flowchart of a method for monitoring a quality of hydraulic fluid in an EH valve, in accordance with certain implementations of the present disclosure.

FIG. 3 illustrates a flowchart 300 of a method for monitoring the quality of the hydraulic fluid in the EH valve 108, in accordance with certain implementations of the present disclosure. The flowchart 300 will be described in conjunction with FIG. 1 and FIG. 2.

At step 302, the predetermined dither signal may be applied to the solenoid coil 248 in the EH valve 108 to generate an acoustic wave. In certain implementations, the controller 110 may be configured to apply the predetermined dither signal to the solenoid coil 248. The predetermined dither signal may facilitate the oscillation of the pusher pin 224 and the spool 230 to change the static friction to dynamic friction. Thereafter, the controller 110 may apply the actuation signal, superimposed on the predetermined dither signal, to operate the EH valve 110 in a predetermined configuration. Therefore, the predetermined dither signal may be applied to the solenoid coil 248, continuously, irrespective of the configuration in which the EH valve 108 may operate. For example, the controller 110 may apply the actuation signal of the first magnitude to the solenoid coil 248 to operate the EH valve 108 in the first configuration. As discussed, the controller 110 may superimpose the actuation signal on the predetermined dither signal. The EH valve 108, in the first configuration, may allow the hydraulic fluid to flow from the first fluid path 210 to the third fluid path 214. During operation of the EH valve 108 in the first configuration, the hydraulic fluid may flow into the gap 238. When the operation of the hydraulic driven component needs to be halted, the controller 110 may apply the actuation signal (superimposed on the predetermined dither signal) of the second magnitude to operate the EH valve 108 in the second configuration. As discussed, in the second configuration, the EH valve 108 may block the fluid flow between the first fluid path 210 and the third fluid path 214. Further, in the second configuration, the EH valve 108 may block the fluid flow between the third fluid path 214 and the second fluid path 212. Therefore, there may be no fluid movement inside the EH valve 108, when the EH valve 108 operates in the second configuration.

When the EH valve 108 operates in the second configuration, at step 304, the quality of the hydraulic fluid (retained in the gap 238) may be determined based on one or more characteristics of the acoustic wave. In certain implementations, the controller 110 may be configured to determine the quality of the hydraulic fluid. As discussed, the controller 110 may apply the predetermined dither signal continuously (irrespective of the configuration in which the EH valve 108 operates) for continuous oscillation of the pusher pin 224 and the spool 230 to change the static friction to dynamic friction. The oscillation of the pusher pin 224 and the spool 230 may generate the acoustic wave that may propagate through the hydraulic fluid in the gap 238. In some implementations, one or more characteristics of the acoustic wave, propagating through the hydraulic fluid, may vary based on the presence of impurities in the hydraulic fluid. Therefore, the quality of the hydraulic fluid may be determined based on the one or more characteristics of the acoustic wave. In certain implementations, the one or more characteristics of the acoustic wave may include an amplitude of the acoustic wave, a frequency of the acoustic wave, and/or a phase of the acoustic wave.

The acoustic wave may be detected by the acoustic sensor 244 (positioned on the second end wall 208). The acoustic sensor 244 may generate and transmit a voltage signal, corresponding to the detected acoustic wave, to the controller 110. The controller 110 may determine the one or more characteristics of the acoustic wave based on the voltage signal. In some implementations, the controller 110 may determine the quality of the hydraulic fluid based on the determined one or more characteristics of the acoustic wave. The determination of the quality of the hydraulic fluid will further be described in conjunction with FIG. 4.

It may be observed that the quality of the hydraulic fluid is monitored when the EH valve 108 operates in the second configuration, due to the lack of hydraulic fluid flow through the EH valve 108.

Figure 4A:
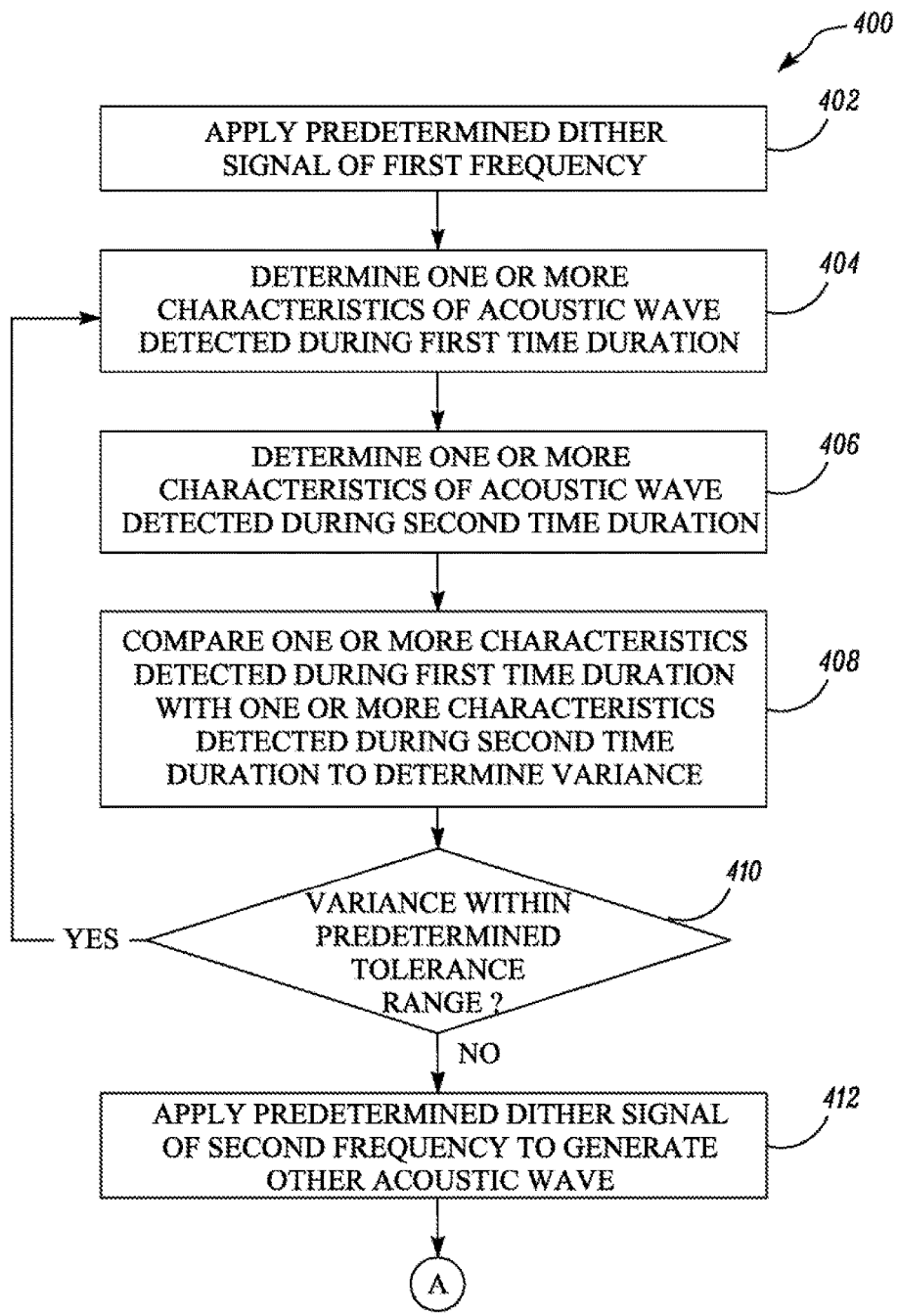
FIG. 4a illustrates a flowchart of another method for monitoring quality of hydraulic fluid in an EH valve, in accordance with certain implementations of the present disclosure.
Figure 4B:
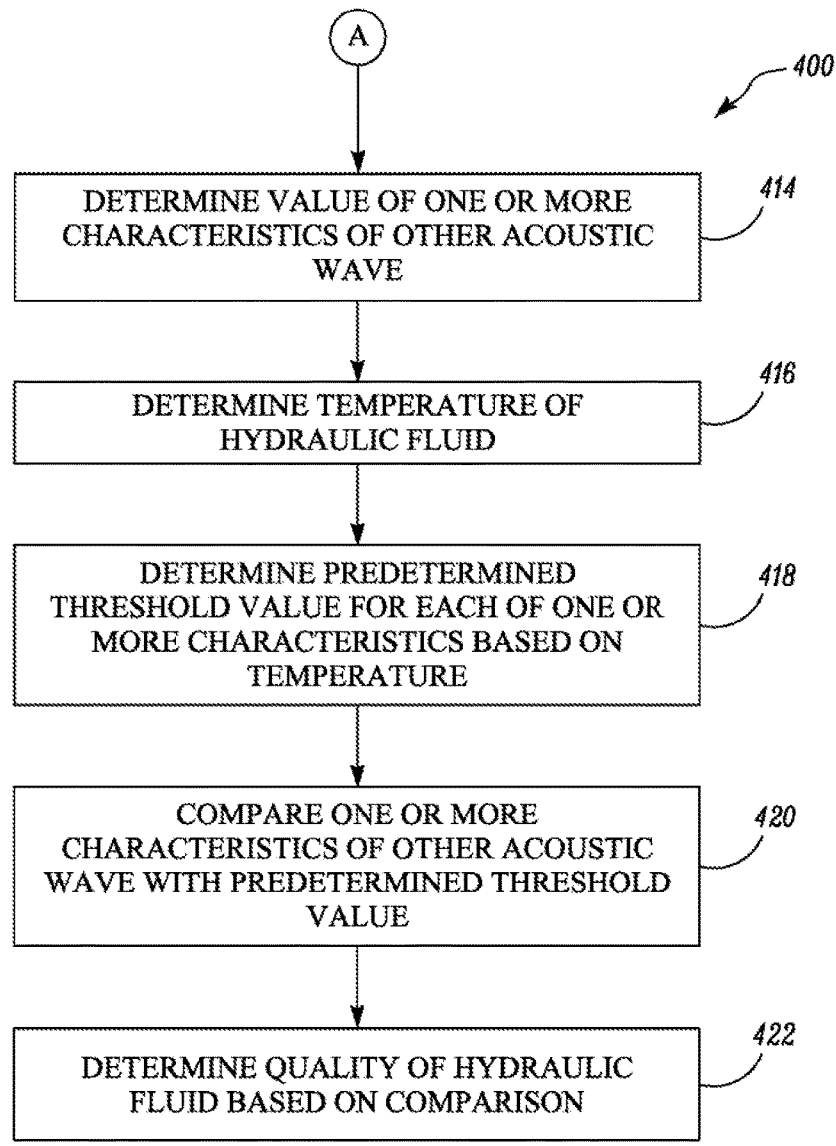
FIG. 4b further illustrates a flowchart of another method for monitoring quality of hydraulic fluid in an EH valve, in accordance with certain implementations of the present disclosure.

FIG. 4 illustrates a flowchart 400 of another method for monitoring the quality of the hydraulic fluid in the EH valve 108, in accordance with certain implementations of the present disclosure. The flowchart 400 may be described in conjunction with FIG. 1, FIG. 2 and FIG. 3.

At step 402, the predetermined dither signal of a first frequency may be applied to the solenoid coil 248. In certain implementations, the controller 110 may be configured to apply the predetermined dither signal of the first frequency. For example, the controller 110 may apply the predetermined dither signal of 1 KHz to the solenoid coil 248. Upon application of the predetermined signal, the armature 222 may oscillate at the first frequency that in turn may cause the pusher pin 224 to oscillate. Further, the oscillation of the pusher pin 224 may reciprocate the oscillation of the spool 230. As discussed, the oscillation of the pusher pin 224 and the spool 230 may change the static friction to dynamic friction. In certain implementations, the dynamic friction may minimize the hysteresis and therefore may improve the response of EH valve 108. Further, the oscillation of the pusher pin 224 and the spool 230 may facilitate generation of the acoustic wave. The acoustic wave may propagate through the hydraulic fluid in the gap 238.

At step 404, the one or more characteristics associated with the acoustic wave, detected during a first time duration, may be determined. In some implementations, the controller 110 may be configured to determine the one or more characteristics of the acoustic wave detected during the first time duration. Hereinafter, the one or more characteristics of the acoustic wave detected during the first time duration have been referred to as one or more first characteristics. In some implementations, the one or more first characteristics of the acoustic wave may correspond to a value of each of the one or more characteristics of the acoustic wave detected during the first time duration. For example, the controller 110 may determine the value of the frequency, the value of the phase, and/or the value of the amplitude as the one or more first characteristics of the acoustic wave detected during the first time duration.

Prior to determining the one or more first characteristics of the acoustic wave, the controller 110 may instruct the acoustic sensor 244 to detect the acoustic wave during the first time duration. The acoustic sensor 244 may generate the voltage signal corresponding to the detection of the acoustic wave during the first time duration. In some implementations, the controller 110 may receive the voltage signal from the acoustic sensor 244. In some implementations, a value of one or more characteristics of the voltage signal may be proportional to a value of the one or more characteristics of the acoustic wave detected by the acoustic sensor 244. For example, the amplitude of the voltage signal may be proportional to amplitude of the acoustic wave. Similarly, the frequency of the voltage signal may be proportional to the frequency of the acoustic wave. Based on the one or more characteristics of the voltage signal, the controller 110 may determine the one or more first characteristics of the acoustic wave detected during the first time duration. In some implementations, the controller 110 may utilize the proportional relationship between the one or more characteristics of the voltage signal and the one or more characteristics of the acoustic signal, to determine the one or more first characteristics of the acoustic signal.

At step 406, the one or more characteristics associated with the acoustic wave, detected during a second time duration, may be determined. In some implementations, the controller 110 may be configured to determine the one or more characteristics of the acoustic wave detected during the second time duration, in a manner similar to that described above with respect to step 404. Hereinafter, the one or more characteristics of the acoustic wave detected during the second time duration have been referred to as one or more first characteristics. In some implementations, the one or more second characteristics may correspond to a value of each of the one or more characteristics of the acoustic wave detected during the second time duration. In some implementations, the first time duration and the second time duration may be consecutive time durations.

In some implementations, the first time duration and the second time duration may be determined based on a predefined sample period. In certain implementations, the predefined sample period may correspond to a time duration during which the one or more characteristics of the acoustic wave may be monitored. Further, a time instant from which the acoustic sensor 244 may have to detect the acoustic wave may be determined based on a predefined sample rate. For example, if the predefined sample rate is 10 samples per minute and the predefined sample period is six seconds, the controller 110 may instruct the acoustic sensor 244 to start detection of the acoustic wave at the first second of the minute for six seconds. Thereafter, the controller 110 may instruct the acoustic sensor 244 to start detection of the acoustic wave at the seventh second of the minute for next six seconds.

At step 408, the one or more characteristics of the acoustic wave detected during the first time duration (i.e., the one or more first characteristics) may be compared with the one or more characteristics of the acoustic wave detected during the second time duration (i.e., the one or more second characteristics), to determine a variance. In certain implementations, the controller 110 may be configured to perform the comparison. In certain implementations, the controller 110 may be further configured to determine a variance between the one or more first characteristics and the one or more second characteristics of the acoustic wave detected during the first time duration and during the second time duration, respectively, based on the comparison. For example, the controller may be configured to determine a difference between the one or more first characteristics and the one or more second characteristics. As the one or more first characteristics and the one or more second characteristics correspond to the value of the one or more characteristics of the acoustic wave detected during the first time duration and the second time duration, respectively, the variance may correspond to a variation in the value of each of the one or more characteristics of the acoustic wave detected during the first time duration and the second time duration. For example, if the frequency of the acoustic wave detected during the first time duration is 500 Hz and the frequency of the acoustic wave detected during the second time duration is 750 Hz, the variance in the value of the frequency at two consecutive time durations is 50%.

In certain implementations, the variance in the value of the one or more characteristics may be indicative of impurities in the hydraulic fluid. The impurities may correspond to suspended particles that may be in a random motion in the hydraulic fluid. Such suspended particles may cause variation in the value of the one or more characteristics of the acoustic wave. Such variations may be recorded during determination of the variance in the value of the one or more characteristics of the acoustic wave.

Additionally, or optionally, the controller 110 may further determine the temperature of the hydraulic fluid during the determination of the variance. The temperature of the hydraulic fluid may be utilized to derive the viscosity of the hydraulic fluid. In some implementations, variation in the viscosity of the hydraulic fluid may cause variation of the one or more characteristics of the acoustic wave (propagating through the hydraulic fluid). Therefore, during the determination of the variance, the controller 110 may determine the temperature of the hydraulic fluid to derive the viscosity of the hydraulic fluid. For example, the controller 110 may determine a first viscosity of the hydraulic fluid based on a temperature of the hydraulic fluid determined during the first time duration. Further, the controller 110 may determine a second viscosity of the hydraulic fluid based on the temperature of the hydraulic fluid determined during the second time duration. Thereafter, the controller 110 may normalize the one or more first characteristics and the one or more second characteristics based on the first viscosity and the second viscosity, respectively, according to a standard temperature and pressure condition applicable during EH valve 108 operation. Thereafter, the controller 110 may determine the variance based on the normalized one or more first characteristics and the normalized one or more second characteristics.

At step 410, a check may be performed to determine whether the determined variance of each of the one or more characteristics is within a predetermined tolerance range (or predetermined range). In certain implementations, the controller 110 may be configured to perform the check. In certain implementations, the tolerance range of the variance may be determined during calibration of the acoustic sensor 244.

If at step 410, the controller 110 determines that the variance determined for each of the one or more characteristics is within the predetermined tolerance range, the controller 110 may repeat the step 404. If at the step 410 the controller 110 determines that the variance is not within the predetermined tolerance range, the controller 110 may perform the step 412. For example, if the predetermined tolerance range is ±5% and the variance in the value of the frequency of the acoustic wave during two consecutive time durations is 10%, the controller 110 may determine that the variance is not in the tolerance range of ±5%. Therefore, the controller 110 may proceed to step 412. In certain implementations, the tolerance range may be defined separately for each of the one or more characteristics of the acoustic wave. In alternative implementations, a common tolerance range may be defined for the one or more characteristics of the acoustic wave.

At step 412, the predetermined dither signal of a second frequency may be applied to the solenoid coil 248. In certain implementations, the controller 110 may be configured to apply the predetermined dither signal of the second frequency to the solenoid coil 248. The application of the predetermined dither signal of the second frequency may modify the frequency of oscillation of the pusher pin 224 and the spool 230. In certain implementations, the pusher pin 224 and the spool 230 may oscillate at the second frequency. In certain implementations, the second frequency of the predetermined dither signal is greater than the first frequency of the predetermined dither signal.

As discussed, the oscillation of the spool 230 may facilitate generation of another acoustic wave that propagates through the hydraulic fluid in the gap 238. The acoustic sensor 244 may detect the other acoustic wave propagating through the hydraulic fluid in the gap 238.

At step 414, a value of the one or more characteristics of the other acoustic wave may be determined. In certain implementations, the controller 110 may be configured to determine the value of the one or more characteristics of the other acoustic wave. In certain implementations, the controller 110 may employ similar methodologies, as described in the step 404, to determine the value of the one or more characteristics of the other acoustic wave.

As the frequency of the other acoustic wave (generated by the predetermined dither signal of second frequency) is greater than the frequency of the acoustic wave (generated by the predetermined dither signal of first frequency), the other acoustic wave is more immune to the noise in comparison to the immunity of the acoustic wave to the noise. Therefore, even if there an error in the determination of the one or more first characteristics and/or the one or more second characteristics at steps 404 and/or 406 (due to noise), the generation of the other acoustic wave of higher frequency ensures that the value of the one or more characteristics of the other acoustic wave is less erroneous.

At step 416, the temperature of the hydraulic fluid may be determined. In certain implementations, the controller 110 may be configured to determine the temperature of the hydraulic fluid. In certain implementations, the controller 110 may receive a voltage signal from the temperature sensor 246 (positioned on the second end wall 208 of the cavity 204). The controller 110 may determine the temperature of the hydraulic fluid based on the voltage signal received from the temperature sensor 246.

At step 418, a predetermined threshold value for each of the one or more characteristics may be determined based on the value of the temperature. In certain implementations, the controller 110 may be configured to determine the predetermined threshold value. The controller 110 may utilize a look up table to determine the predetermined threshold value for each of the one or more characteristics. In certain implementations, the lookup table may comprise the threshold values of each of the one or more characteristics corresponding to one or more temperature ranges. For example, for a temperature range between 50° C.-100° C., the corresponding threshold value of the frequency of the acoustic wave may be 6 Khz. Similarly, the threshold value for other one or more characteristics may be defined in the lookup table corresponding to other temperature ranges.

The controller 110 may search the determined temperature of the hydraulic fluid in the lookup table to identify a relevant temperature range. For example, the lookup table includes temperature ranges as 50° C.-100° C., 100° C.-150° C., and 150° C.-200° C. If the measured temperature of the hydraulic fluid is 145° C., the controller 110 may select the temperature range as 100° C.-150° C. Thereafter, the controller 110 may determine the threshold values for each of the one or more characteristics defined for the selected temperature range (100° C.-150° C.).

At step 420, the value of the one or more characteristics of the other acoustic wave may be compared with the predetermined threshold values of the respective one or more characteristics. In certain implementations, the controller 110 may be configured to perform the comparison of the value of the one or more characteristics of the other acoustic with the respective threshold values to determine whether the value of the one or more characteristics of the other acoustic wave exceed the predetermined threshold values.

At step 422, the quality of the hydraulic fluid may be determined based on the comparison of the value of each of the one or more characteristics of the other acoustic wave with the threshold value of the respective one or more characteristics. In certain implementations, the controller 110 may be configured to determine the quality of the hydraulic fluid. If the controller 110 determines that the value of each of the one or more characteristics of the other acoustic wave has exceeded the respective threshold values, the controller 110 may determine that the quality of the hydraulic fluid has degraded and needs replacement. In some implementations, the controller 110 may determine that the value of at least one characteristic of the other acoustic wave has exceeded the respective threshold value, the controller 110 may determine that the quality of the hydraulic oil has degraded. In other implementations, the controller 110 may assign a weight to each of the one or more characteristics. In certain implementations, the weight may be indicative of an importance assigned to each of the one or more characteristics. For example, the impurities in the hydraulic fluid may more effect the amplitude of acoustic wave in comparison to the frequency of the hydraulic fluid. Therefore, the weight assigned to the amplitude may be more in comparison to the frequency of the acoustic signal. In certain implementations, the weights assigned to each of the one or more characteristics may vary based on a type of the hydraulic fluid being used in the EH valve 108.

After assigning the weight to each of the one or more characteristics, the controller 110 may identify characteristics that have exceeded the respective threshold value. The controller 110 may assign a value '1' to the identified characteristics. Thereafter, the controller 110 may multiply the value '1' with the respective weights and determine a weighted sum of the one or more characteristics. The controller 110 may compare the weighted sum with a threshold value of the weighted sum. Based on the comparison of the weighted sum with the threshold value, the controller 110 may determine the quality of the hydraulic oil. For example, if the weighted sum has exceeded the threshold value of the weighted sum, the controller 110 may determine that the quality of the hydraulic fluid has degraded.

At step 424, a notification may be transmitted to an output device. In certain implementations, the controller 110 may be configured to transmit the notification. In certain implementations, the output device may correspond to an audio device or a display device or a LED. In a scenario, where the output device is the audio device, the notification may correspond to an audio signal. In a scenario, where the output device corresponds to the display device, the notification may correspond to a warning message that may be displayed on the display device. In a scenario, where the output device corresponds to the LED, the notification may correspond to voltage signal that may switch the LED to an ON state.

INDUSTRIAL APPLICABILITY

Figure 5:
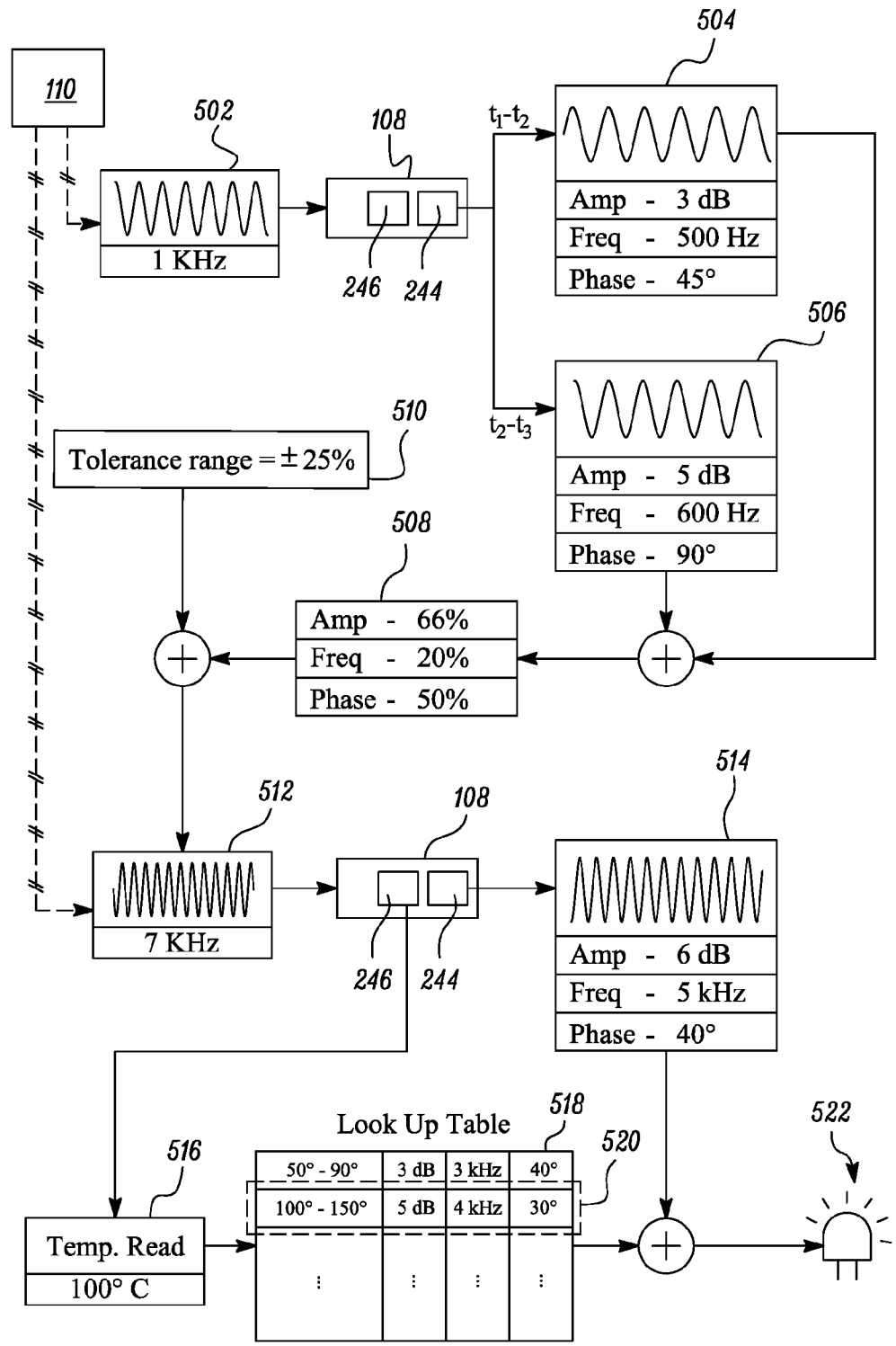
FIG. 5 illustrates an exemplary flow diagram to determine the quality of the hydraulic fluid used in an EH valve, in accordance with certain implementations of the present disclosure.

FIG. 5 illustrates an exemplary flow diagram 500 to determine the quality of the hydraulic fluid used in the EH valve 108, in accordance with certain implementations. The exemplary flow diagram 500 will be described in conjunction with FIG. 2, FIG. 3, and FIG. 4.

The controller 110 may apply the predetermined dither signal (represented by 502) of 1 KHz to the EH valve 108. In certain implementations, the predetermined dither signal may correspond to a dither signal that is used to keep the pusher pin 224 in the EH valve 8 in motion (e.g., oscillation) to improve the EH valve 108 response. As discussed above, the oscillation of the pusher pin 224 generates the acoustic wave that propagates through the hydraulic fluid in the gap 238. The acoustic sensor 244 detects the acoustic wave during two consecutive time durations $t_1$-$t_2$ and $t_2$-$t_3$ (depicted by 504 and 506, respectively).

The controller 110 determines the one or more characteristics of the acoustic wave detected during the two time durations (depicted by 504 and 506, respectively). For example, the controller 110 may determine the one or more first characteristics of the acoustic wave detected during the time duration $t_1$-$t_2$ (depicted by 504) as:
Amplitude: 3 db;
Frequency: 500 Hz; and
Phase: 45°.

Similarly, the controller 110 may determine the one or more second characteristics of the acoustic wave detected during the time duration $t_2$-$t_3$ (depicted by 506) as:
Amplitude: 5 db;
Frequency: 600 Hz; and
Phase: 90°.

Thereafter, the controller 110 determines the variance (depicted by 508) between the one or more first characteristics and the one or more second characteristics. For example, the controller 110 may determine following variance:
Variance in amplitude: 66%;
Variance in frequency: 20%; and
Variance in phase: 50%.

After determination of the variance between the one or more first characteristics and the one or more second characteristics, the controller 110 compare the determined variance with the predetermined tolerance range of ±25% (depicted by 510). The controller 110 determines that the variance of the frequency is within the predetermined tolerance range. However, the variance in the amplitude and the variance in the phase are not in the predetermined tolerance range. Therefore, the controller 110 applies the predetermined dither signal of 7 KHz frequency to the EH valve (depicted by 512) to validate the detection of the variance in the one or more characteristics of the acoustic wave during two consecutive time durations $t_1$-$t_2$ and $t_2$-$t_3$ (depicted by 504 and 506, respectively). On application of the predetermined dither signal of 7 KHz, the oscillation of the pusher pin 224 generates another acoustic signal that propagates through the hydraulic fluid in the gap 238. The acoustic sensor 244 detects the other acoustic wave and the controller 110 may accordingly determine the one or more characteristics of the other acoustic wave (depicted by 514). For example, the controller 110 determines the one or more characteristics of the other acoustic wave as:
Amplitude of the other acoustic wave: 6 db
Frequency of the other acoustic wave: 5 Khz
Phase of the other acoustic wave: 40°

Concurrently, the temperature sensor 246 determines the temperature of the hydraulic fluid as 100° C. (depicted by 516). Thereafter, the controller 110 searches in the lookup table 518 to identify the range of temperature values in which the determined temperature lies in. From the FIG. 5, it can be observed that controller 110 identifies the temperature range 100° C.-150° C. (depicted by 520). Further, the controller 110 extracts the predetermined threshold values of the one or more characteristics corresponding to the temperature range 100° C.-150° C. (depicted by 520). From the lookup table 518, it can be observed that the controller 110 extracts the following predetermined threshold values (depicted by 520) for the one or more characteristics:
Predetermined threshold value for amplitude: 5 db;
Predetermined threshold value for frequency: 4 Khz; and
Predetermined threshold value for phase: 30°.

Thereafter, the controller 110 compares the one or more characteristics of the other acoustic signal (depicted by 514) with the predetermined threshold values of the respective one or more characteristics (depicted by 520) to determine whether the value of the one or more characteristics exceed the predetermined threshold value (depicted by 520). For example, the controller 110 determine that the value of the amplitude of the other acoustic wave (depicted by 514) exceeds the predetermined threshold value of the amplitude (depicted by 520). Further, the controller 110 determines that the frequency of the other acoustic wave (depicted by 514) exceeds the predetermined threshold value of the frequency (depicted by 520).

As the controller 110 determines that the value of each of the one or more characteristics of the other acoustic wave (depicted by 514) exceed the threshold value of the respective one or more characteristics (depicted by 520), the controller 110 generates a notification signal that is indicative of the quality of the hydraulic fluid. In certain implementations, the controller 110 generates a voltage signal (as the notification signal) that turns on a LED to indicate that the quality of the hydraulic fluid has deteriorated and the hydraulic fluid needs replacement. In certain implementations, LED switches ON when the voltage signal is received (depicted by 522).

As the predetermined dither signal generates acoustic wave, therefore, a need to have separate acoustic wave generator may be avoided. Further, as the quality of the hydraulic fluid is being monitored during the operation of the hydraulic system, the real time quality of the hydraulic fluid is being determined. Additionally, as the quality of the hydraulic fluid is monitored in two steps (first when the predetermined dither signal of first frequency is applied and the second when the predetermined dither signal of second frequency is applied), the high accuracy in determination of the quality of the hydraulic fluid is achieved.

While aspects of the present disclosure have been particularly shown and described with reference to certain implementations above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A method for monitoring a quality of a hydraulic fluid in an electro-hydraulic (EH) valve, the method comprising:
   applying a predetermined signal to a solenoid coil, surrounding a pusher pin in the EH valve, to facilitate oscillation of the pusher pin to change static friction, between the pusher pin and a cavity of the EH valve, to dynamic friction,
   the EH valve comprising a housing defining the cavity,
   the cavity having an end wall,
   the cavity slidably receiving the pusher pin,
   the pusher pin having a first end and a second end,
   the hydraulic fluid being received between the first end of the pusher pin and the end wall,
   the oscillation of the pusher pin generating an acoustic wave that propagates through the hydraulic fluid; and
   determining the quality of the hydraulic fluid based on one or more characteristics of the acoustic wave detected by an acoustic sensor positioned on the end wall.

2. The method of claim 1, wherein the housing of the EH valve defines one or more fluid paths, wherein the quality of the hydraulic fluid is determined when the EH valve operates in a configuration where each of the one or more fluid paths are fluidly decoupled one from another.

3. The method of claim 1, wherein the predetermined signal, applied to the solenoid coil, is of a first frequency.

4. The method of claim 3 further comprising:
   detecting the acoustic wave during a first time duration;
   detecting the acoustic wave during a second time duration,
   wherein the one or more characteristics of the acoustic wave include one or more first characteristics of the acoustic wave detected during the first time duration and one or more second characteristics of the acoustic wave detected during the second time duration,
   wherein the first time duration and the second time duration are consecutive time durations, and
   wherein the one or more characteristics of the acoustic wave comprise an amplitude of the acoustic wave, a frequency of the acoustic wave, and a phase of the acoustic wave.

5. The method of claim 4 further comprising:
   comparing the one or more first characteristics of the acoustic wave with the one or more second characteristics of the acoustic wave, and
   determining whether a variance between the one or more first characteristics of the acoustic wave and the one or more second characteristics of the acoustic wave is within a tolerance range, the variance being determined based on the comparison.

6. The method of claim 5, wherein a predetermined signal of a second frequency is applied to the solenoid coil based on determining whether the variance is within the tolerance range, wherein the predetermined signal of the second frequency facilitates generation of another acoustic wave based on the oscillation of the pusher pin, and wherein the other acoustic wave propagates through the hydraulic fluid to the acoustic sensor.

7. The method of claim 6, wherein the quality of the hydraulic fluid is determined based on a comparison of one or more characteristics of the other acoustic wave with a predetermined threshold value of a corresponding characteristic.

8. The method of claim 7 further comprising determining, by a temperature sensor disposed in the cavity, a temperature of the hydraulic fluid, wherein the predetermined threshold value of the corresponding characteristic is determined based on the temperature of the hydraulic fluid.

9. An electro-hydraulic (EH) valve comprising:
   a housing defining a cavity having an end wall;
   a pusher pin slidably received in the cavity, the pusher pin having a first end and a second end, wherein the first end of the pusher pin is proximate to the end wall, wherein a hydraulic fluid is received between the first end of the pusher pin and the end wall;
   an acoustic sensor disposed on the end wall; and
   a solenoid coil surrounding the pusher pin, wherein an actuation of the solenoid coil controls a movement of the pusher pin in the cavity, the solenoid coil being configured to receive a predetermined signal to facilitate oscillation of the pusher pin to change static friction between the pusher pin and the cavity, to dynamic friction,
   wherein the oscillation of the pusher pin generates an acoustic wave that propagates through the hydraulic fluid,
   wherein the acoustic sensor is configured to detect the acoustic wave through the hydraulic fluid, and
   wherein a controller determines a quality of the hydraulic fluid based on one or more characteristics of the acoustic wave detected by the acoustic sensor.

10. The EH valve of claim 9, wherein the pusher pin has a first portion and a second portion, wherein the first portion corresponds to a spool proximate to the end wall, and wherein the second portion of the pusher pin is surrounded by the solenoid coil.

11. The EH valve of claim 9, wherein the housing further defines one or more fluid paths, wherein a position of the pusher pin in the cavity controls fluid communication among the one or more fluid paths.

12. The EH valve of claim 9, wherein the predetermined signal, applied to the solenoid coil, is of a first frequency.

13. The EH valve of claim 12, wherein the acoustic wave is detected during a first time duration, wherein the acoustic wave is detected during a second time duration, wherein the one or more characteristics of acoustic wave include one or more first characteristics of the acoustic wave detected during the first time duration, and one or more second characteristics of the acoustic wave detected during the second time duration, wherein the first time duration and the second time duration are consecutive time durations.

14. The EH valve of claim 13, wherein the controller compares the one or more first characteristics of the acoustic wave with the one or more second characteristics of the acoustic wave, to determine a variance between the one or more first characteristics and the one or more second characteristics.

15. The EH valve of claim 14, wherein the controller applies the predetermined signal of a second frequency to the solenoid coil based on a determination whether the variance is within a tolerance range, wherein the predetermined signal of the second frequency facilitates generation of another acoustic wave based on the oscillation of the pusher pin, wherein the other acoustic wave propagates through the hydraulic fluid to the acoustic sensor.

16. The EH valve of claim 15, wherein the controller compares the one or more characteristics of the other acoustic wave with a predetermined threshold value of corresponding characteristic to determine the quality of the hydraulic fluid.

17. The EH valve of claim 15 further comprising a temperature sensor, disposed in the cavity between the first end of the pusher pin and the end wall, configured to measure a temperature of the hydraulic fluid, wherein the predetermined threshold value of each of the one or more characteristics is determined based on the temperature of the hydraulic fluid.

18. An electro-hydraulic (EH) valve system for monitoring a quality of a hydraulic fluid used in the EH valve system, the EH valve system comprising:
an EH valve comprising:
a housing defining a cavity having an end wall,
a pusher pin slidably received in the cavity, the pusher pin having a first end and a second end, wherein the first end of the pusher pin is proximate to the end wall, wherein the hydraulic fluid is received between the first end of the pusher pin and the end wall,
an acoustic sensor disposed on the end wall, and
a solenoid coil surrounding the pusher pin, wherein an actuation of the solenoid coil controls a movement of the pusher pin in the cavity; and
a controller communicatively coupled to the acoustic sensor, the controller being configured to:
apply a predetermined signal to the solenoid coil to facilitate oscillation of the pusher pin to change static friction between the pusher pin and the cavity, to dynamic friction, wherein the oscillation of the pusher pin generates an acoustic wave that propagates through the hydraulic fluid,
receive a voltage signal, from the acoustic sensor, corresponding to the acoustic wave detected by the acoustic sensor,
determine one or more characteristics of the acoustic wave based on one or more characteristics of the voltage signal, and
determine the quality of the hydraulic fluid based on the one or more characteristics of the acoustic wave.

19. The EH valve system of claim 18, wherein the controller is further configured to determine one or more first characteristics of the acoustic wave detected during a first time duration and one or more second characteristics of the acoustic wave detected during a second time duration, wherein the first time duration and the second time duration are consecutive time durations, and wherein the one or more first characteristics and the one or more second characteristics constitute the one or more characteristics of the acoustic wave.

20. The EH valve system of claim 19, wherein the controller is further configured to:
compare the one or more first characteristics of the acoustic wave, with the one or more second characteristics of the acoustic wave, and
determine a variance between the one or more first characteristics and the one or more second characteristics based on the comparison, wherein the quality of the hydraulic fluid is determined based at least on the variance.

* * * * *